United States Patent
Guo et al.

(10) Patent No.: US 9,624,176 B2
(45) Date of Patent: Apr. 18, 2017

(54) METHOD FOR PREPARING CAPROLACTAM BY USING A MICROREACTOR UNDER LEWIS ACID CATALYSIS

(71) Applicant: NANJING TECH UNIVERSITY (CN), Nanjing (CN)

(72) Inventors: Kai Guo, Nanjing (CN); Xin Li, Nanjing (CN); Zheng Fang, Nanjing (CN); Kai Zhang, Nanjing (CN); Qi Yu, Nanjing (CN); Pingkai Ouyang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 15/192,869

(22) Filed: Jun. 24, 2016

(65) Prior Publication Data

US 2017/0008850 A1    Jan. 12, 2017

(30) Foreign Application Priority Data

Jul. 8, 2015   (CN) .......................... 2015 1 0398873

(51) Int. Cl.
  *C07D 201/04*   (2006.01)
  *C07D 201/06*   (2006.01)
  *C07D 223/10*   (2006.01)

(52) U.S. Cl.
  CPC ............ *C07D 223/10* (2013.01); *Y02P 20/52* (2015.11)

(58) Field of Classification Search
  CPC ........................... C07D 201/04; C07D 201/06
  See application file for complete search history.

(56) References Cited

U.S. PATENT DOCUMENTS 3,687,938 A * 8/1972 Masaki ................ C07D 211/76
                                                    540/451

\* cited by examiner

*Primary Examiner* — Bruck Kifle
(74) *Attorney, Agent, or Firm* — CBM Patent Consulting, LLC

(57) ABSTRACT

A method for preparing caprolactam by using a microreactor under Lewis acid catalysis, wherein a hydroxyl group in a cyclohexanone oxime is activated to obtain a cyclohexanone oxime sulfonates intermediate, then rearranged under Lewis acid catalysis to prepare the caprolactam. The method of this invention has a simple process and a high operation safety and selectivity, the reaction condition is mild, an efficient reaction can take place even at room temperature, the reaction time is short, the conversion of the cyclohexanone oxime can reach 100% within a short time, the selectivity of the caprolactam can reach 99%, the energy consumption is greatly reduced in the premise of maintaining a high yield, and the production cost is reduced, being an efficient and green and environmentally friendly method of for synthesizing the caprolactam.

9 Claims, 1 Drawing Sheet

METHOD FOR PREPARING CAPROLACTAM BY USING A MICROREACTOR UNDER LEWIS ACID CATALYSIS

This application claims priority to Chinese Patent Application Ser. No. 6 CN201510398873.7 filed 8 Jul. 2015.

FIELD OF THE INVENTION

The present invention belongs to the technical field of chemical synthesis, and more specifically relates to a method for preparing caprolactam by using a microreactor under Lewis acid catalysis.

BACKGROUND OF THE INVENTION

Caprolactam is an important monomer for making polyamide-6 fiber, plastics and thin film. The production of caprolactam in China is not sufficient to meet the production requirement of the domestic market. Up to 2010, the total apparent consumption of caprolactam in China has exceeded 1.1 million tons, but the self-sufficiency rate is only 43.9%. At present, about 90% of the total production of caprolactam in the world adopts a liquid-phase Beckmann rearrangement process of cyclohexanone oxime using concentrated sulfuric acid or fuming sulfuric acid as a catalyst. Although this route has a selectivity of 98% or more, there are many problems such as heavy environmental pollution, serious equipment corrosion, generation of a large amount of byproduct ammonium sulphate with low value.

At present, there are many methods under research for preparing caprolactam without the byproduct of ammonium sulphate. At present, they are mainly gas-phase Beckmann rearrangement and liquid-phase rearrangement processes using a solid catalyst. But these processes usually have many problems such as the preparation cost of the solid catalyst being too high, the selectivity of the caprolactam being too low, or the catalyst being prone to inactivation and the effectiveness of reuse being too poor, thereby greatly limiting its industrialized application.

A microreactor is a three-dimensional structural element which can be used in chemical reaction and made of a solid substrate by means of a special microfabrication technology. The microreactor generally has a small channel size (its equivalent diameter being smaller than 500 µm) and a channel diversity, a fluid flows in these channels, and requires a desired reaction to take place in these channels. This causes that a chemical equipment with microstructure has a very large specific surface area to volume ratio, resulting in an extremely high mass transfer and heat transfer capacity. Fundamental advantages due to this is an extremely high heat exchange efficiency and mixing efficiency, and that the reaction temperature can be precisely controlled and the reaction materials can be instantaneously mixed in a precise mix proportion, they are key factors for increasing yield, selectivity, safety and improving product quality. At present, the application of the microreactor in the technical field of chemical synthesis is still in a new research stage, and the research of the application of the microreactor in studying the preparation of caprolactam by Beckmann rearrangement is also still in laboratory study stage. Luo Guangsheng, Zhang Jisong et al. of Tsinghua University prepared caprolactam in a microreactor by using fuming sulfuric acid or organic acid as the catalyst, its process can rapidly and efficiently synthesize caprolactam within a extremely short time, the conversion is up to 99.9% or more, and the selectivity is also greater than 99%. This demonstrates that the application of the microreactor in preparation of caprolactam has a great application prospect. But, these reactions usually require high temperature and high pressure and catalysis by a strong acid medium, thereby limiting their industrialized application to a certain extent or increasing the cost of industrialized application. Therefore, searching for methods for preparing caprolactam under a relatively mild condition and their application in industrial production is also hot subjects of current research.

SUMMARY OF THE INVENTION

The problem to be solved by this invention is to provide a method for preparing caprolactam by using a microreactor under Lewis acid catalysis, in order to resolve the problems of low reaction selectivity and catalyst being prone to inactivation existing in the prior art.

To resolve the above-mentioned technical problem, a technical solution adopted by this invention is as follow:

A method for preparing caprolactam by using a microreactor under Lewis acid catalysis, it comprises the following steps:

(1) cyclohexanone oxime is dissolved in an organic solvent, an organic acid binding agent is added, and homogeneously mixed, to obtain a homogeneous solution;

(2) a sulfonyl chlorides compound is dissolved in an organic solvent, and homogeneously mixed, to obtain a homogeneous solution;

(3) a Lewis acid is dissolved in an organic solvent, and homogeneously mixed, to obtain a homogeneous solution;

(4) the homogeneous solution obtained in step (1) and the homogeneous solution obtained in step (2) are concurrently and respectively pumped into a first microchannel reactor in a microreactor, and completely reacted, to obtain a cyclohexanone oxime sulphonates intermediate;

(5) the mixed system obtained in step (4) and the homogeneous solution obtained in step (3) are concurrently and respectively pumped into a second microchannel reactor of the microreactor, and completely reacted, then an outflow liquid is collected, to obtain the caprolactam.

In step (1), the organic solvent is acetonitrile, toluene, DMSO or dichloromethane, and the organic acid binding agent is pyridines acid binding agent and organic amines acid binding agent; wherein, the pyridines organic acid binding agent is preferably pyridine, and the organic amines organic acid binding agent is triethylamine or ethylenediamine.

In the homogeneous solution obtained in step (1), the concentration of the cyclohexanone oxime is 0.2-3.0 mol/L, and the concentration of the organic acid binding agent is 0.3-5.0 mol/L.

In step (2), the sulfonyl chlorides compound is any one of sulfonyl chloride, methanesulfonyl chloride, benzenesulfonyl chloride, p-toluenesulfonyl chloride, and p-nitrobenzenesulfonyl chloride or a combination thereof, the organic solvent is acetonitrile, toluene, DMSO or dichloromethane; in the homogeneous solution obtained in step (2), the concentration of the sulfonyl chlorides compound is 0.2-3.0 mol/L.

In step (3), the Lewis acid is anhydrous aluminum chloride, boron trifluoride diethyl etherate, iron trichloride, stannic chloride or zinc chloride, preferably anhydrous aluminum trichloride, boron trifluoride diethyl etherate or iron trichloride; the organic solvent is acetonitrile, toluene, DMSO or dichloromethane; in the homogeneous solution obtained in step (3), the concentration of the Lewis acid is 0.4-5.0 mol/L.

Wherein, the reaction mole ratio of the cyclohexanone oxime, the organic acid binding agent and the sulfonyl chlorides compound is 1:1-2.5:1-1.5, and the reaction mole ratio of the cyclohexanone oxime sulphonates intermediate and the Lewis acid is 1:1-5.

Wherein, in the first microchannel reactor of step (4), the reaction temperature is 25-50° C., and the reaction residence time is 5-20 minutes; wherein, the flow rate for pumping the homogeneous solution obtained in step (1) into the first microchannel reactor is 0.1-2.0 ml/min, and the flow rate for pumping the homogeneous solution obtained in step (2) into the first microchannel reactor is 0.15-2.5 ml/min.

Wherein, in the second microchannel reactor of step (5), the reaction temperature is 25-50° C., the reaction residence time is 5-25 min; wherein, the flow rate for pumping the homogeneous solution obtained in step (3) into the second microchannel reactor is 0.5-3.0 ml/min, and the flow rate for pumping the mixed system obtained in step (4) into the second microchannel reactor is 0.25-4.5 ml/min.

Wherein, the volume of the first microchannel reactor is 5-15 ml, and the volume of the second microchannel reactor is 5-25 ml.

Wherein, the microreactor comprises a feed liquid inlet, a first T-mixing valve, a first microchannel reactor, a second T-mixing valve, a second microchannel reactor and a liquid outlet which are connected in series successively by connection tubes, the detailed assembly is as shown in FIG. 1.

Wherein, a front end of the first T-mixing valve is connected to a feed inlet for the homogeneous solutions in step (1) and step (2), a back end is connected to an inlet of the first microchannel reactor;

a front end of the second T-mixing valve is connected to an outlet of the first microchannel reactor and a feed inlet for the homogeneous solution in step (3), a back end is connected to an inlet of the second microchannel reactor.

Wherein, the diameter of the connection tubes are all 0.1-20 mm.

Wherein, the length of the connection tube between the feed liquid inlet and the microchannel reactor is 10-50 cm;

The length of the connection tube between of the first microchannel reactor and the second microchannel reactor is 10-50 cm;

The length of the connection tube between the second microchannel reactor and the liquid outlet is 10-70 cm.

Wherein, the preferred type of the microchannel reactor is Vapourtec R series, purchased form Tegent International Scientific Ltd Co.

Wherein, the reaction formula of this invention is as follow:

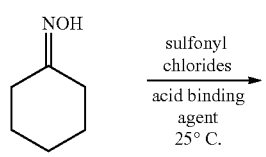

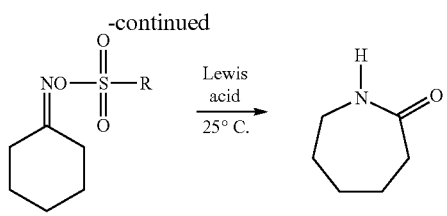

Beneficial Effects:

Compared with the prior art, the microreactor has such characteristics as large specific surface area, high transfer velocity, short contact time, less byproduct, very high heat transfer and mass transfer capacity, fast, direct scale-up, high safety, good operability; the microreactor system is a parallel system with a modular structure, it has a characteristic of good portability. Making use of an efficient mixing performance and an excellent mass transfer and heat transfer characteristics of the microchannel reactor, the cyclohexanone oxime is converted into a cyclohexanone oxime sulphonates intermediate in the first reactor, then the caprolactam is generated under the Lewis acid catalysis in the second reactor, this method has a simple process and a high operation safety and selectivity, its reaction condition is mild, an efficient reaction can take place even at room temperature, the reaction time is short, the conversion of the cyclohexanone oxime can reach 100% within a short time, the selectivity of caprolactam can reach 99%, the energy consumption is greatly reduced and the production cost is reduced in the premise of maintaining a high yield, being an efficient and green and environmentally friendly method for synthesizing caprolactam, and having an industrialized application prospect.

DETAILED DESCRIPTION OF THE EMBODIMENTS

This invention can be better understood based on the following examples. However, a person skilled in the art will readily understand that, the content described in the examples is only used to illustrate this invention, and should not and will not limit the invention described in detail in the claims.

Figure 1:
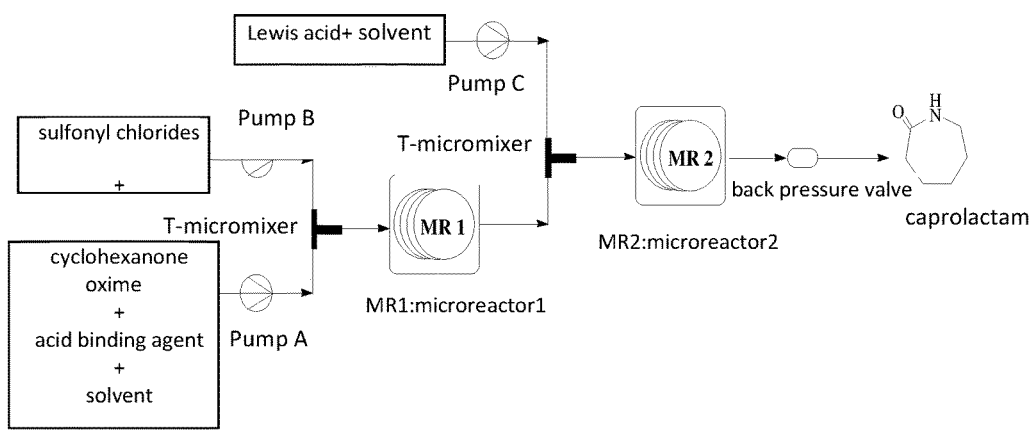
FIG. 1 is a structural schematic diagram of the microreactor of this invention.
Figure 2:
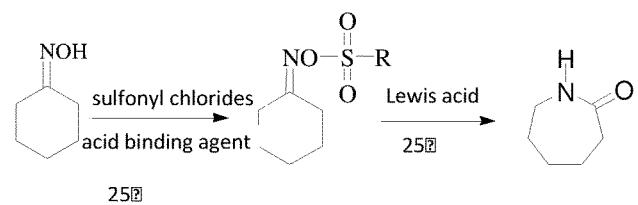
FIG. 2 is a reaction formula of this invention.

The following microreactor consists of a feed liquid inlet, a T-micromixer, microchannel reactors 1 and 2 (heating devices are disposed externally), a back pressure regulator and a liquid outlet etc. which are connected successively by connection tubes, the detailed assembly is as shown in FIG. 1, wherein two reaction material containers are connected to respective feed liquid inlet by the connection tubes and respectively connected to a T-micromixer, and a pump A and a pump B are respectively disposed in the connection tubes, the T-micromixer is connected to the microchannel reactor 1 by a connection tube, connection tubes of a third reaction material container are respectively connected to the T-micromixer via a pump C and an outlet pipe of the microchannel reactor 1, and enters into the microchannel reactor 2, and the microchannel reactor 2 is connected to the back pressure regulator, finally connected to a liquid outlet pipe. The cyclohexanone oxime, the acid binding agent, the Lewis acid, and the sulfonyl chlorides compound used in the experiment are all CP, the organic solvent is AR.

Example 1

In the microchannel reactor, the diameter of the connection tubes are all 1 mm, the length of the liquid inlet pipes are all 15 cm, the length of the connection tubes between the T-valve and the microchannel reactor 1 and 2 are both 30 cm, the length of connection tube between the microchannel reactor 1 and the outlet is 20 cm, the length of the connection tube between the microchannel reactor 2 and the outlet is 30 cm; the volume of the microchannel reactor 1 is 5 ml, the volume of the microchannel reactor 2 is 20 ml.

1.15 g cyclohexanone oxime (purity 98%) and 1.13 g triethylamine (purity 98%) were added into a certain volume of acetonitrile, to obtain a homogeneous solution in which the concentration of the cyclohexanone being 1.0 mol/L and the concentration of the triethylamine being 1.1 mol/L, and it was pumped into the microchannel reactor 1 by the pump A, the volume flow rate in the pump A was controlled to 0.25 ml/min; 2. 2.85 g p-toluenesulfonyl chloride was added into a certain volume of acetonitrile, the concentration of the p-toluenesulfonyl chloride was 1.0 mol/L, and pumped into the microchannel reactor 1 at a flow rate of 0.25 ml/min by the pump B, such that the reaction mole ratio of the cyclohexanone oxime, the triethylamine and the p-benzenesulfonyl chloride was 1:1.1:1, the temperature of the microreactor was controlled to 25° C., the reaction residence time was 10 min; 3. 2.5 g iron trichloride (purity 97%) was dissolved with a certain volume of acetonitrile, a 1.5 mol/L iron trichloride solution was obtained, this solution and the solution from the microchannel reactor 1 were pumped by the pump C at a flow rate of 0.5 ml/min through the T-micromixer and into the microchannel reactor 2, such that the theoretical mole ratio of iron trichloride and cyclohexanone oximesulphonate intermediate was kept at 3:1, the temperature of the microreactor 2 was controlled to 25° C., the reaction residence time was 20 minutes; 4. sampled, detected by High Performance Liquid Chromatography, and the conversion of the cyclohexanone oxime and the selectivity of the caprolactam were calculated, the conversion of the cyclohexanone was 100%, the selectivity of the caprolactam was 99.0%.

Example 2

The microreactor is substantially same as Example 1, the only difference is: in the microchannel reactor, the diameter of the connection tubes are all 1.2 mm, the length of the liquid inlet pipes are all 10 cm, the length of the connection tube between the T-valve and the microchannel reactor 1 is 30 cm, the length of the connection tube between another T-mixing valve and the microchannel reactor 2 is 40 cm, the length of the connection tube between the microchannel reactor 1 and the outlet is 30 cm, the length of the connection tube between the microchannel reactor 2 and the outlet is 50 cm; the volume of the microchannel reactor 1 is 10 ml, the volume of the microchannel reactor 2 is 24 ml.

0.57 g cyclohexanone oxime (purity 98%) and 1.03 g triethylamine (purity 98%) were added into a certain volume of acetonitrile, to obtain a homogeneous solution in which the concentration of the cyclohexanone being 0.5 mol/L and the concentration of the triethylamine being 1.0 mol/L, and it was pumped into the microchannel reactor 1 by the pump A, the volume flow rate in the pump A was controlled to 0.5 ml/min; 2. 1.0 g benzenesulfonyl chloride was added into a certain volume of acetonitrile, the concentration of the benzenesulfonyl chloride was 0.55 mol/L, and pumped into the microchannel reactor 1 at a flow rate of 0.5 ml/min by the pump B, such that the reaction mole ratio of the cyclohexanone oxime, the triethylamine and the benzenesulfonyl chloride was 1:2:1.1, the temperature of the microreactor 2 was controlled to 40° C., the reaction residence time was 10 min; 3. 1.1 g iron trichloride (purity 97%) was dissolved in a certain volume of acetonitrile, an iron trichloride solution of 0.625 mol/L was obtained, this solution and the solution from the microchannel reactor 1 were pumped at a flow rate of 0.6 ml/min by the pump C through the T-micromixer and into the microchannel reactor 2, such that the theoretical mole ratio of the iron trichloride and the cyclohexanone oxime sulphonate intermediate was maintained at 1.5:1, the temperature of the microreactor 2 was controlled to 40° C., the reaction residence time was 15 minutes; 4. sampled, and detected by High Performance Liquid Chromatography, the conversion of the cyclohexanone oxime and the selectivity of the caprolactam were calculated, the conversion of the cyclohexanone oxime was 99.9%, the selectivity of caprolactam was 92.6%.

Example 3

The microreactor is substantially same as Example 1, the only difference is: in the microchannel reactor, the diameter of the connection tubes are all 1 mm, the length of the liquid inlet pipes are all 15 cm, the length of the connection tube between the T-valve and the microchannel reactor 1 is 25 cm, the length of a connection tube between another T-mixing valve and the microchannel reactor 2 is 30 cm, the length of a connection tube between of the microchannel reactor 1 and the outlet is 20 cm, the length of a connection tube between the microchannel reactor 2 and the outlet is 50 cm; the volume of the microchannel reactor is 15 ml, the volume of microchannel reactor 2 is 15 ml.

0.23 g cyclohexanone oxime (purity 98%) and 0.27 g pyridine (purity 98%) were added into a certain volume of acetonitrile, a homogeneous solution in which the concentration of the cyclohexanone being 0.2 mol/L and the concentration of the pyridine being 0.34 mol/L was obtained, and it was pumped into the microchannel reactor 1 by the pump A, the volume flow rate in the pump A was controlled to 0.5 ml/min; 2. 0.40 g sulfonyl chloride was added into a certain volume of acetonitrile, the concentration of the sulfonyl chloride was 0.3 mol/L, and pumped into the microchannel reactor 1 at a flow rate of 0.5 ml/min by the pump B, such that the reaction mole ratio of the cyclohexanone oxime, the pyridine and the sulfonyl chloride was 1:1.7:1.5, the temperature of the microreactor 1 was controlled to 50° C., the reaction residence time was 5 minutes; 3. 0.568 g boron trifluoride diethyl etherate (purity 97%) was dissolved in a certain volume of acetonitrile, and a boron trifluoride diethyl etherate solution of 0.4 mol/L was obtained, this solution and the solution from the microchannel reactor 1 were pumped at a flow rate of 0.5 ml/min by the pump C through the T-micromixer and into the microchannel reactor 2, such that the theoretical mole ratio of the boron trifluoride and the cyclohexanone oxime sulphonate intermediate was maintained at 2:1, the temperature of the microreactor 2 was controlled to 25° C., the reaction residue time was 10 minutes; 4. sampled, detected by High Performance Liquid Chromatography, and the conversion of the cyclohexanone oxime and the selectivity of caprolactam were calculated, the conversion of the cyclohexanone oxime was 100%, the selectivity of caprolactam was 91.3%.

Example 4

The microreactor is substantially same as Example 1, the only difference is: in the microchannel reactor, the diameter of the connection tubes are all 1.6 mm, the length of the liquid inlet pipes are all 30 cm, the length of the connection tube between the T-valve and the microchannel reactor 1 is 30 cm, the length of the connection tube between another T-micromixer and the microchannel reactor 2 is 40 cm, the length of the connection tube between the microchannel reactor 1 and the outlet is 35 cm, the length of the connection tube between the microchannel reactor 2 and the outlet is 70 cm; the volume of the microchannel reactor 1 is 5 ml, the volume of the microchannel reactor 2 is 10 ml.

2.3 g cyclohexanone oxime (purity 98%) and 4.12 g triethylamine (purity 98%) were added into a certain volume of acetonitrile, a homogeneous solution in which the concentration of cyclohexanone being 2.0 mol/L and the concentration of triethylamine being 4.0 mol/L was obtained, and it was pumped into the microchannel reactor 1 by the pump A, the volume flow rate in the pump A was controlled to 0.10 ml/min; 2. 1.98 g methanesulfonyl chloride was added into a certain volume of acetonitrile, the concentration of the methanesulfonyl chloride was 1.73 mol/L, and pumped into the microchannel reactor 1 at a flow rate of 0.15 ml/min by the pump B, such that the reaction mole ratio of the cyclohexanone oxime, the triethylamine and the methanesulfonyl chloride was 1:2:1.3, the temperature of the microreactor 1 was controlled to 35° C., the reaction residence time was 20 minutes; 3. 2.2 g aluminum trichloride (purity 97%) was dissolved in a certain volume of acetonitrile, an aluminum trichloride solution of 1.6 mol/L was obtained, this solution and the solution from the microchannel reactor 1 were pumped at a flow rate of 0.25 ml/min by the pump C through the T-micromixer and into the microchannel reactor 2, such that the theoretical mole ratio of the aluminum trichloride and the cyclohexanone oxime sulphonate intermediate was kept at 2:1, the temperature of the microreactor 2 was controlled to 35° C., the reaction residence time was 20 minutes; 4. sampled, detected by High Performance Liquid Chromatography, and the conversion of the cyclohexanone oxime and the selectivity of the caprolactam were calculated, the conversion of the cyclohexanone oxime was 100%, the selectivity of the caprolactam was 95.7%.

Example 5

The microreactor is substantially same as Example 1, the only difference is: in the microchannel reactor, the diameter of the connection tubes are all 2 mm, the length of the liquid inlet pipes are all 50 cm, the length of the connection tube between the T-valve and the microchannel reactor 1 is 35 cm, the length of the connection tube between another T-mixing valve and the microchannel reactor 2 is 50 cm, the length of the connection tube between the microchannel reactor 1 and the outlet is 30 cm, the length of the connection tube between the microchannel reactor 2 and the outlet is 70 cm; the volume of microchannel reactor 1 is 10 ml, the volume of the microchannel reactor 2 is 25 ml.

1.03 g cyclohexanone oxime (purity 98%) and 1.74 g pyridine (purity 98%) were added into a certain volume of acetonitrile, a homogeneous solution in which the concentration of the cyclohexanone being 0.9 mol/L and the concentration of the pyridine being 2.16 mol/L, and the solution was pumped into the microchannel reactor 1 by the pump A, the volume flow rate in the pump A was controlled to 1.0 ml/min; 2. 2.1 g p-toluenesulfonyl chloride was added into a certain volume of acetonitrile, the concentration of the p-toluenesulfonyl chloride was 1.08 mol/L, and pumped into the microchannel reactor 1 at a flow rate of 1.0 ml/min by the pump B, such that the reaction mole ratio of the cyclohexanone oxime, the pyridine and the p-toluenesulfonyl chloride was 1:2.4:1.2, the temperature of the microreactor 1 was controlled to 25° C., the reaction residence time was 5 minutes; 3. 5.34 g iron trichloride (purity 97%) was dissolved in a certain volume of acetonitrile, an iron trichloride solution of 3.2 mol/L was obtained, this solution and the solution from the microchannel reactor 1 were pumped at a flow rate of 1.12 ml/min by the pump C through the T-mixer and into the microchannel reactor 2, such that the theoretical mole ratio of the iron trichloride and the cyclohexanone oxime sulphonate intermediate was kept at 4:1, the temperature of the microreactor 2 was controlled to 25° C., the reaction residence time was 8 minutes; 4. sampled, detected by High Performance Liquid Chromatography, and the conversion of the cyclohexanone oxime and the selectivity of the caprolactam were calculated, the conversion of the cyclohexanone oxime was 100%, and the selectivity of caprolactam was 94.1%.

What is claimed is:

1. A method for preparing caprolactam by using a microreactor under Lewis acid catalysis, comprising the following steps:
   (1) cyclohexanone oxime is dissolved in an organic solvent, an organic acid binding agent is added, and homogeneously mixed, to obtain a homogeneous solution;
   (2) a sulfonyl chlorides compound is dissolved in an organic solvent, and homogeneously mixed, to obtain a homogeneous solution;
   (3) a Lewis acid is dissolved in an organic solvent, and homogeneously mixed, to obtain a homogeneous solution;
   (4) the homogeneous solution obtained in step (1) and the homogeneous solution obtained in step (2) are concurrently and respectively pumped into a first microchannel reactor of a microreactor, and completely reacted, to obtain a cyclohexanone oxime sulphonates intermediate;
   (5) a mixed system obtained in step (4) and the homogeneous solution obtained in step (3) are concurrently and respectively pumped into a second microchannel reactor of the microreactor, and completely reacted, a outflow liquid is collected, to obtain the caprolactam.

2. The method for preparing caprolactam by using a microreactor under Lewis acid catalysis according to claim 1, characterized in that, in step (1), the organic solvent is acetonitrile, toluene, DMSO or dichloromethane, and the organic acid binding agent is pyridines acid binding agent and organic amines acid binding agent.

3. The method for preparing caprolactam by using a microreactor under Lewis acid catalysis according to claim 1, characterized in that, in the homogeneous solution obtained in step (1), the concentration of the cyclohexanone oxime is 0.2-3.0 mol/L, and the concentration of the organic acid binding agent is 0.3-5.0 mol/L.

4. The method for preparing caprolactam by using a microreactor under Lewis acid catalysis according to claim 1, characterized in that, in step (2), the sulfonyl chlorides compound is any one of sulfonyl chloride, methanesulfonyl chloride, benzenesulfonyl chloride, p-tolunesulfonyl chloride and p-nitrobenbenzenesulfonyl chloride or a combination thereof, the organic solvent is acetonitrile, toluene, DMSO or dichloromethane; in the homogeneous solution obtained in step (2), the concentration of the sulfonyl chlorides compound is 0.2-3.0 mol/L.

5. The method for preparing caprolactam by using a microreactor under Lewis acid catalysis according to claim 1, characterized in that, in step (3), the Lewis acid is anhydrous aluminum chloride, boron trifluoride diethyl etherate, iron trichloride, stannic chloride or zinc chloride; the organic solvent is acetonitrile, toluene, DMSO or dichloromethane; in the homogeneous solution obtained in step (3), the concentration of the Lewis acid is 0.4-5.0 mol/L.

6. The method for preparing caprolactam by using a microreactor under Lewis acid catalysis according to claim 1, characterized in that, a reaction mole ratio of the cyclohexanone oxime, the organic acid binding agent and the sulfonyl chlorides compound is 1:1-2.5:1-1.5, and the reaction mole ratio of the cyclohexanone oxime sulphonates intermediate and the Lewis acid is 1:1-5.

7. The method for preparing caprolactam by using a microreactor under Lewis acid catalysis according to claim 1, characterized in that, in the first microchannel reactor of step (4), the reaction temperature is 25-50° C., the reaction residence time is 5-20 minutes; wherein, the flow rate for pumping the homogeneous solution obtained in step (1) into the first microchannel reactor is 0.1-2.0 ml/min, the flow rate for pumping the homogeneous solution obtained in step (2) into the first microchannel reactor is 0.15-2.5 ml/min.

8. The method for preparing caprolactam by using a microreactor under Lewis acid catalysis according to claim 1, characterized in that, in the second microchannel reactor of step (5), the reaction temperature is 25-50° C., the reaction residence time is 5-25 minutes; wherein, the flow rate for pumping the homogeneous solution obtained in step (3) into the second microchannel reactor is 0.5-3.0 ml/min, the flow rate for pumping the mixed system obtained in step (4) into the second microchannel reactor is 0.25-4.5 ml/min.

9. The method for preparing caprolactam by using a microreactor under Lewis acid catalysis according to claim 1, characterized in that, the volume of the first microchannel reactor is 5-15 ml, and the volume of the second microchannel reactor is 5-25 ml.

* * * * *